US009408619B2

(12) United States Patent
Salehi et al.

(10) Patent No.: US 9,408,619 B2
(45) Date of Patent: *Aug. 9, 2016

(54) LOW PROFILE PATIENT SPECIFIC CUTTING BLOCKS FOR A KNEE JOINT

(71) Applicant: Smith & Nephew, Inc., Memphis, TN (US)

(72) Inventors: Abraham Biglari Salehi, Barlett, TN (US); David Timothy Mehl, Memphis, TN (US); Mark Ellsworth Nadzadi, Memphis, TN (US); Aashiish Agnihotri, Memphis, TN (US); Jason Sean Jordan, Hernando, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/642,116

(22) Filed: Mar. 9, 2015

(65) Prior Publication Data
US 2015/0182238 A1 Jul. 2, 2015

Related U.S. Application Data

(63) Continuation of application No. 12/920,645, filed as application No. PCT/US2009/035935 on Mar. 3, 2009, now Pat. No. 9,033,991.

(60) Provisional application No. 61/033,419, filed on Mar. 3, 2008, provisional application No. 61/089,373, filed on Aug. 15, 2008.

(51) Int. Cl.
A61B 17/56 (2006.01)
A61B 17/17 (2006.01)
A61B 17/15 (2006.01)

(52) U.S. Cl.
CPC ........... A61B 17/1764 (2013.01); A61B 17/155 (2013.01); A61B 17/157 (2013.01)

(58) Field of Classification Search
CPC ... A61B 17/151; A61B 17/154; A61B 17/157

USPC ...................... 606/86 R, 87–89, 96
See application file for complete search history.

(56) References Cited

U.S. PATENT DOCUMENTS 5,514,140 A 5/1996 Lackey
5,720,752 A 2/1998 Elliott et al.
(Continued)

FOREIGN PATENT DOCUMENTS

CN 1184409 A 6/1998
CN 101878002 A 11/2010
(Continued)

OTHER PUBLICATIONS

Australian Patent Examination Report No. 1; Australian Patent Office; Australian Patent Application No. 2009221920; Apr. 16, 2013; 2 pages.
(Continued)

Primary Examiner — Anu Ramana
(74) Attorney, Agent, or Firm — Taft Stettinius & Hollister LLP

(57) ABSTRACT

A low profile patient specific cutting block for a knee comprises a plurality of bone interfacing portions and a cutting slot. The plurality of bone interfacing portions are configured to overlie portions of an end of a bone. The bone interfacing portions each have a surface generally a negative of the portion of the bone the bone interfacing portion overlies. The bone interfacing portions are angularly offset from each other such that a first of the bone interfacing portions overlies an anterior portion of the bone and a second of the bone interfacing portions overlies a portion of bone generally perpendicular to the anterior portion of bone. The cutting slot is oriented in a fixed position relative to the bone interfacing portions such that the cutting slot directs a cutting tool at a fixed angle and at a fixed depth from the bone interfacing portions.

20 Claims, 3 Drawing Sheets

(56) References Cited

U.S. PATENT DOCUMENTS

| | | |
|---|---|---|
| 7,104,997 B2 | 9/2006 | Lionberger et al. |
| 8,323,288 B2 | 12/2012 | Zajac |
| 8,343,159 B2 | 1/2013 | Bennett |
| 8,357,166 B2 | 1/2013 | Aram et al. |
| 8,361,076 B2 | 1/2013 | Roose et al. |
| 8,377,068 B2 | 2/2013 | Aker et al. |
| 8,398,645 B2 | 3/2013 | Aker et al. |
| 8,419,740 B2 | 4/2013 | Aram et al. |
| 2007/0100462 A1 | 5/2007 | Lang et al. |
| 2008/0015599 A1 | 1/2008 | D'Alessio et al. |
| 2009/0087276 A1 | 4/2009 | Rose |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Rose et al. |
| 2009/0088763 A1 | 4/2009 | Aram et al. |
| 2009/0093816 A1 | 4/2009 | Roose et al. |

FOREIGN PATENT DOCUMENTS

| | | |
|---|---|---|
| JP | 07-222751 A | 8/1995 |
| JP | 2006-510403 | 3/2006 |
| JP | 2008-523962 | 7/2008 |
| WO | 9400056 A1 | 1/1994 |
| WO | 02096268 | 12/2002 |
| WO | 02096271 A2 | 12/2002 |
| WO | 2004049981 | 6/2004 |
| WO | 2006069260 | 6/2006 |
| WO | 2006078511 A1 | 7/2006 |
| WO | 2007092841 A2 | 8/2007 |
| WO | 2007097853 A2 | 8/2007 |
| WO | 2007097854 | 8/2007 |
| WO | 2007097854 A2 | 8/2007 |

OTHER PUBLICATIONS

Chinese Patent Office, Chinese First Office Action dated Feb. 4, 2013, 7 pages (with translation).

Chinese Second Office Action; State Intellectual Property Office of People's Republic of China; Dec. 16, 2013; Chinese Patent Application No. 200990108374.2; 6 pages.

First European Office Action; European Patent Office; European Patent Application No. 09716515.3; Jan. 27, 2014; 6 pages.

Second European Office Action; European Patent Office; European Patent Application No. 09716515.3; Jan. 8, 2015, 4 pages.

Japanese Patent Office; Japanese First Office Action; May 28, 2013; 9 pages.

Second Japanese Office Action; Japanese Patent Office; Japanese Patent Application No. 2010-549835; Mar. 3, 2014; 6 pages.

Third Japanese Office Action; Japanese Patent Office; Japanese Patent Application No. 2010-549835; Jan. 5, 2015; 5 pages.

Japanese Decision of Rejection; Japanese Patent Office; Japanese Patent Application No. 2010-549835; Aug. 3, 2015; 4 pages.

European Office Action; European Patent Office; European Patent Application No. 09716515.3; Jan. 27, 2016; 3 pages.

Chinese Search Report; State Intellectual Property Office of People's Republic of China; Chinese Patent Application No. 201410652267.9; Jan. 14, 2016; 5 pages.

Chinese Office Action; State Intellectual Property Office of People's Republic of China; Chinese Patent Application No. 201410652267.9; Jan. 27, 2016; 10 pages.

Australian Examination Report; Australian Patent Office; Australian Patent Application No. 2015202216; Apr. 26, 2016; 2 pages.

LOW PROFILE PATIENT SPECIFIC CUTTING BLOCKS FOR A KNEE JOINT

CROSS-REFERENCE TO RELATED APPLICATIONS

This application is a continuation of U.S. patent application Ser. No. 12/920,645 filed Jan. 5, 2011, which is a U S, national phase filing of International Application No. PCT/US2009/035935 filed Mar. 3, 2009, which claims the benefit of U.S. Provisional Application No. 61/033,419 filed Mar. 3, 2008 and which further claims the benefit of U.S. Provisional Application No. 61/089,373 filed Aug. 15, 2008. The disclosure of each of these applications is incorporated by reference in its entirety.

FIELD OF THE INVENTION

This invention relates generally to cutting blocks for bone resections at a knee joint and, more particularly, for cutting blocks designed for a patient's specific bone and cartilage and further configured to a surgeon's preferences.

SUMMARY OF THE INVENTION

It is in view of problems related to the field above that the present invention was developed.

In one aspect of the invention, a low profile patient specific cutting block for a knee comprises a plurality of bone interfacing portions and a cutting slot. The plurality of bone interfacing portions are configured to overlie portions of an end of a bone. The bone interfacing portions each have a surface generally a negative of the portion of the bone the bone interfacing portion overlies. The bone interfacing portions are angularly offset from each other such that a first of the bone interfacing portions overlies an anterior portion of the bone and a second of the bone interfacing portions overlies a portion of bone generally perpendicular to the anterior portion of bone. The cutting slot is oriented in a fixed position relative to the bone interfacing portions such that the cutting slot directs a cutting tool at a fixed angle and at a fixed depth from the bone interfacing portions.

In another embodiment of the invention the low profile patient specific cutting block is a femoral cutting block. The block further comprises bosses having a thickness and an aperture extending through the bosses. The aperture has a diameter. The bosses are configured to direct a pin through the boss. The thickness of the boss is greater than the diameter of the aperture.

In yet another embodiment, the bone interfacing portions are generally oriented in the middle of the low profile patient specific cutting block in an anterior portion of the low profile patient specific cutting block and are oriented medially and laterally at a posterior portion of the low profile patient specific cutting block.

Alternatively, the low profile patient specific cutting block is a tibial block and the cutting slot is offset and medialized relative to the tibial bone.

Another embodiment includes a paddle extending posteriolaterally from a middle portion of the patient specific cutting block. The paddle has a raised portion anteriorly oriented on the low profile patient specific cutting block such that the paddle does not touch the tibia on an anterior proximal surface and does touch the tibia on a posterior proximal surface.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

DETAILED DESCRIPTION OF THE EMBODIMENTS

Figure 1:
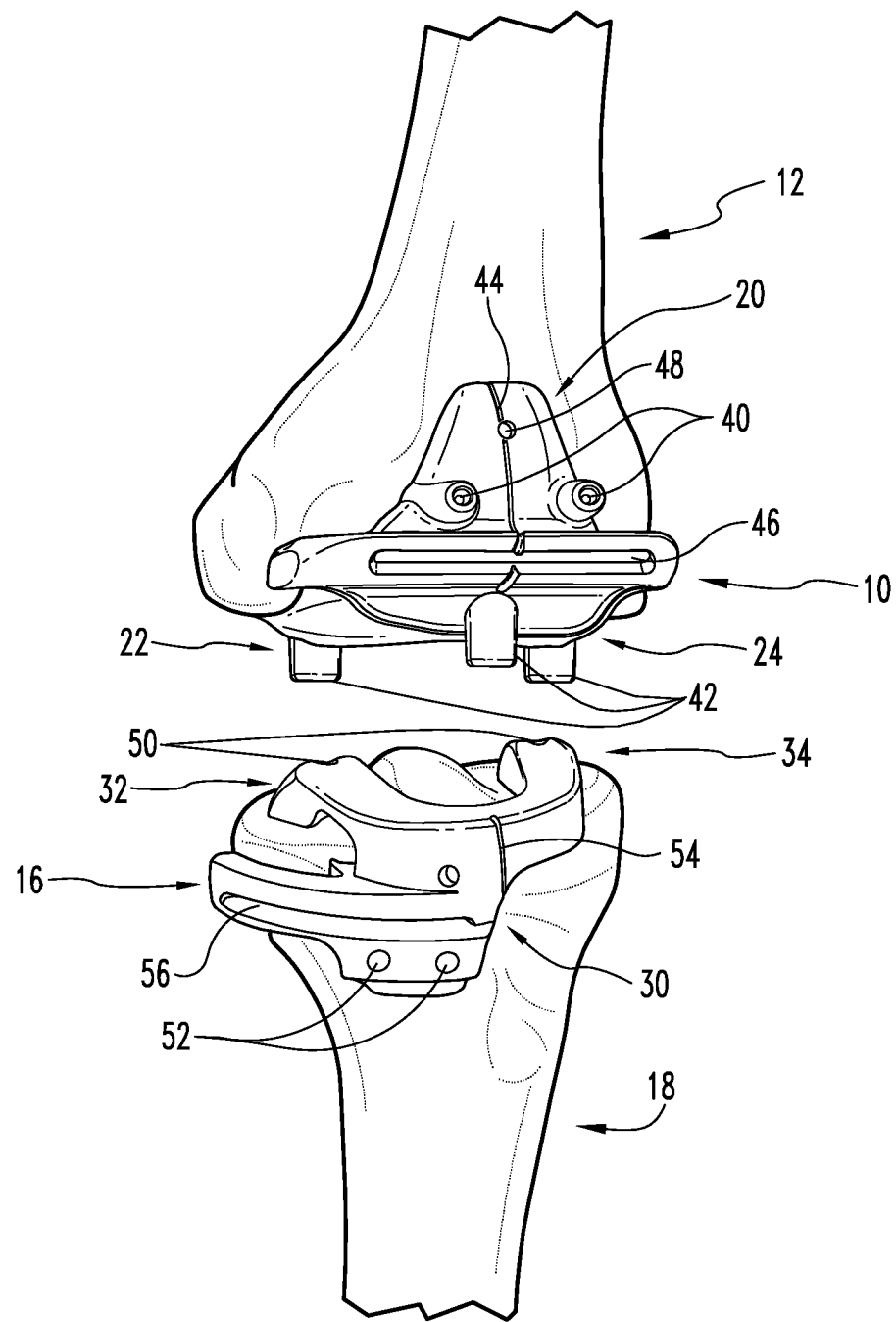
FIG. 1 is a view of a knee joint with a femoral patient specific cutting block and a tibial patient specific block.

Referring to the accompanying drawings in which like reference numbers indicate like elements, FIG. 1 illustrates a view of a knee joint with a femoral patient specific cutting block 10 and a tibial patient specific block 14. The femoral patient specific cutting block 10 is attached to a femur 12. The tibial patient specific cutting block 14 is attached to a tibia 16. The patient specific cutting blocks 10 and 14 are configured to engage portions of bone and cartilage on the femur 12 and tibia 16 to align cutting surfaces within the patient specific cutting blocks so that a distal cut (on the femur) and a proximal cut (on the tibia) may be made without using either intramedullary or extramedullary guides.

The femoral patient specific cutting block 10 includes an anterior femoral portion 20, a medial femoral paddle 22 and a lateral femoral paddle 24. These portions overlie portions of the anterior face, medial condyle and lateral condyle of the femur 12, respectively. Because the portions 20, 22, and 24 only overlie portions of the femur 12 instead of an entire conforming overlay of the end of the femur 12, the patient specific cutting block 10 may have a lower profile, both in the medio-lateral and anterior-posterior direction.

Pin holes 40 and 48, guide bosses 42, a mechanical axis index 44, and a femoral cutting slot 46 are oriented on the exterior surface of the femoral patient specific cutting block 10. The pin holes 40 and 48 are oriented to pin the cutting block 10 to the femur 12. Guide bosses 42 are oriented in order to set pins for the other box cuts necessary to prepare the femur 12 for an implant.

The pin holes 40 and 48 are oriented on the anterior face of the patient specific cutting block 10. The pin holes 40 and 48 may have bosses (as shown with reference to pin holes 40) or may be flush with the surface (as shown with pin hole 48). The bosses may be used to direct the pins, for example, away from the edges of the bone. The low profile of the patient specific cutting block 10 would allow a pin hole without a boss to allow a pin to extend in a wide variety of angular directions. By extending bosses a thickness greater than the diameter of the aperture through the boss, the bosses may orient the pins by adding a guide through the patient specific cutting block 10 so that the pins are directed as they are impacted or drilled into the bone.

The mechanical axis index 44 is oriented along the mechanical axis of the femur 12. A cutting slot 46, oriented relative to anatomical structures and defined by the surgeon, directs the distal cut for an implant. As will be described below, MR and X-rays of the patient are used to align the mechanical axis index 44 to the patient specific cutting block 10.

In addition to the MR and X-ray information, surgeon preferences are used to place the cutting slot 46 on the patient specific cutting block 10. The cutting slot 46 may be oriented relative to the mechanical axis in a varus or valgus orientation (according to surgeon preference based upon the X-ray data). The flexion gap may be adjusted by adjusting the angle of the cutting slot 46 relative to the patient specific cutting block 10. The depth of the resection cut is also determined by the placement of the cutting slot 46 and is determined from the distal point on the condyles.

The guide bosses 42 are also placed on the patient specific cutting block 10 according to MR data, X-ray data and surgeon preference. The guide bosses 42 may set the rotation of the implant by adjusting the posterior bosses 42 relative to one another. The relative placement of the bosses 42 allows for pins to be placed so that the pins guide a further cutting guide over the distal cut of the femur in order to make the anterior and posterior cuts and any chamfer cuts required by the bone interfacing surfaces of the implant. Internal/external rotation is directed by moving the depth of one of the posterior bosses relative to the other posterior boss. A-P placement of the implant is adjusted by moving both of the posterior bosses 42 together in the A-P direction.

The tibial patient specific cutting block 14 includes an anterior femoral portion 300, a medial femoral paddle 32 and a lateral femoral paddle 34. These portions overlie portions of the anterior face, medial plateau and lateral plateau of the tibia 16, respectively. Because the portions 20, 22, and 24 only overlie portions of the tibia 16 instead of an entire conforming overlay of the end of the tibia 16, the patient specific cutting block 14 may have a lower profile, both in the medio-lateral and anterior-posterior direction.

Pin holes 50 and 52, an M-L index 54 and a cutting slot 56 are oriented on the outer surface of the tibial patient specific cutting block 14. The pin holes 50 and 52 may fix the patient specific cutting block 14 to the bone and may additionally align the pins relative to one another for further orientation, if necessary, in tibial preparation.

The tibial cutting slot 56 is medialized relative to the anterior surface of the tibia 16 (i.e., the tibial cutting slot 56 is oriented on the medial half of the anterior side of the patient specific cutting block 14). The lateral paddle 34 may extend around the front of the tibial eminence extending posterior-laterally toward the lateral plateau. These features may allow the guide to be used in a MIS procedure, where lateral clearance is minimized by cutting the tibia from the medial half of the anterior face of the tibia while minimizing the medial approach to the tibia, which would involve additional soft tissue issues. Thus, the medialized and rotated cutting slot 56 is oriented for clearance and accessibility even for an MIS approach.

Figure 2:
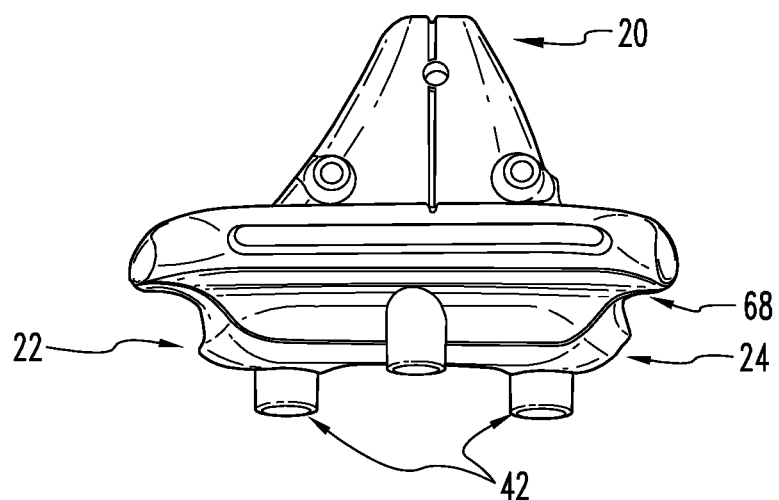
FIG. 2 is an anterior view of a femoral patient specific cutting block according to an aspect of the invention.
Figure 3:
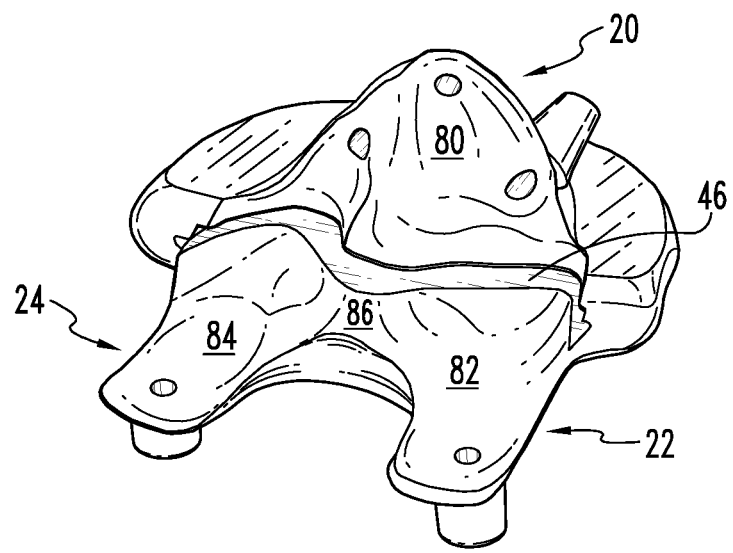
FIG. 3 is a proximal posterior view of a femoral patient cutting specific block according to an aspect of the invention.

Turing now to FIGS. 2 and 3. FIG. 2 is an anterior view of a femoral patient specific cutting block according to an aspect of the invention. FIG. 3 is a proximal posterior view of a femoral patient cutting specific block according to an aspect of the invention. In addition to the features described above, the patient specific cutting block 10 may also include an epicondylar index 68. The epicondylar index 68 may be used as a visual "feel good" for the rotation of the holes and the A-P placement of the holes, similar to the purpose of the mechanical axis index described above.

In FIG. 3, the bone interfacing surfaces 80, 82, 84 and 86 are shown. The anterior bone interfacing portion overlies a portion of the anterior surface of cartilage and bone. The medial bone interfacing portion 82, the lateral bone interfacing portion 84 and the intracondylar bone interfacing portion 86 overlie the medial, lateral and intracondylar notch portions of the condyles, respectively. The bone interfacing portions 80, 82 and 84 align to the anterior and distal faces of the femur while the intracondylar bone interfacing portion 86 orients the block medio-laterally. By using relatively small portions of the surfaces, the profile of the patient specific cutting block 10 may be lowered. Additionally, the fit may be better as smaller portions may result in fewer osteotomes on the bone surface (which may cause poor fit of the patient specific cutting block to the bone. The paddles 22 and 24 may also be relatively thin posteriorly. This further minimizes the profile of the patient specific cutting block.

The cutting slot 46 may be formed through the bone interfacing portions of the patient specific cutting block or may be recessed from the surface. The thickness of the cutting slot helps to direct the orientation of the cutting tool as the cutting tool advances through the cutting slot 46. As previously discussed, the relative angle of the cutting slot 46 to the patient specific cutting block 10 (and particularly to the bone interfacing portions) orients the flexion gap while the translation of the cutting slot 46 relative to the patient specific cutting block 10 sets the resection depth.

Figure 4:
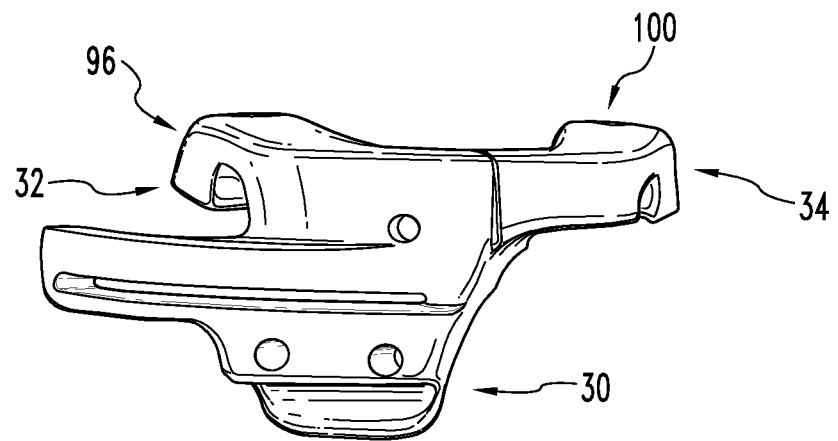
FIG. 4 is an anterior view of a tibial patient specific cutting block according to an aspect of the invention.
Figure 5:
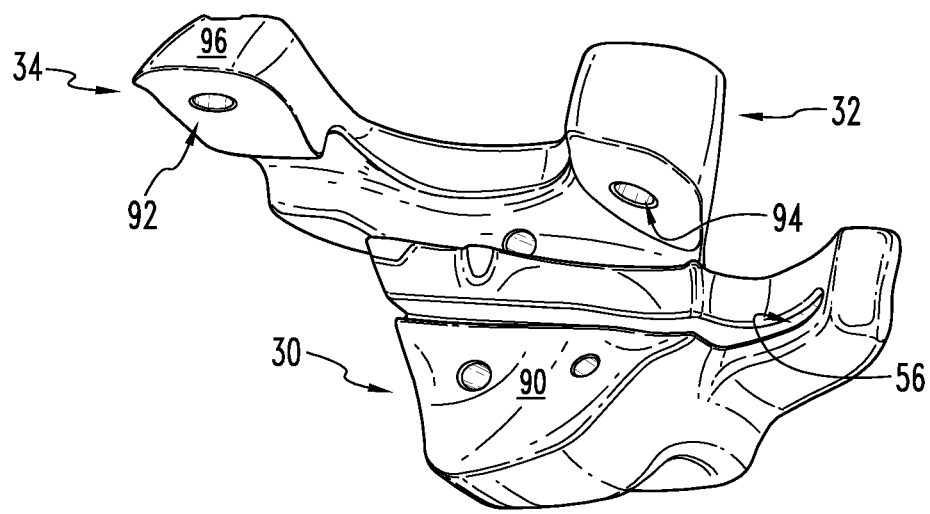
FIG. 5 is a distal posterior view of a tibial patient specific cutting block according to an aspect of the invention.

Turing now to FIGS. 4 and 5, FIG. 4 is an anterior view of a tibial patient specific cutting block according to an aspect of the invention. FIG. 5 is a distal posterior view of a tibial patient specific cutting block according to an aspect of the invention. In addition to the features described above, the tibial patient specific cutting block also may include a posterior chamfer 96 and a planar proximal surface 100. The posterior chamfer 96 allows for the tibial patient specific cutting block to be positioned posteriorly without distracting the soft tissue around the knee more than necessary. Similar to other features, this feature helps the overall profile of the implant.

The planar proximal surface 100 may match the distal femur resection plane from the femoral patient specific cutting block. This feature may allow intraoperative flexion/extension testing when the tibial patient specific cutting block is secured to the tibia.

Bone interfacing surfaces 90, 92, and 94 are shown in FIG. 5. The anterior bone interfacing portion 90 overlies a portion of the anterior surface of cartilage and bone. The medial bone interfacing portion 92 and the lateral bone interfacing portion 84 overlie the medial and lateral portions of the tibia, respectively. The bone interfacing portions 92 and 94 align to the proximal faces of the tibial plateaus (thus orienting the patient specific cutting block proximally) while the anterior bone interfacing portion 90 orients the block medio-laterally and in the AP direction. By using relatively small portions of the surfaces, the profile of the patient specific cutting block may be lowered. Additionally, the fit may be better as smaller portions may result in fewer osteotomes on the bone surface (which may cause poor fit of the patient specific cutting block to the bone. The paddles 32 and 34 may also be relatively thin posteriorly and may be elevated from the tibial plateau surface anteriorly to avoid poor placement. This further minimizes the profile of the patient specific cutting block.

The cutting slot 56 may be formed through the bone interfacing portions of the patient specific cutting block or may be recessed from the surface. If the cutting slot 56 is recessed from the surface, then impingement of the block on bone may be minimized, again increasing the fit of the patient specific cutting block to the bone. The thickness of the cutting slot helps to direct the orientation of the cutting tool as the cutting tool advances through the cutting slot 56. As previously discussed, the relative angle of the cutting slot 56 to the patient specific cutting block 10 (and particularly to the bone interfacing portions) orients the flexion gap while the translation of the cutting slot 46 relative to the patient specific cutting block 10 sets the resection depth.

The MR data and X-ray data may be taken by known means. As an example, the following protocols may be used. Different MR protocols may be executed on different patients. To minimize scan time, a fast spin echo imaging technique may be used for any protocol, essentially producing a proton density (PD) weighted image. One protocol may use the spoiled gradient echo technique with a low repetition time (TR) and low echo time (TE) and a flip angle of 30 degrees combined with a fat saturation technique. A second protocol and third protocol may use a high TR and a low TE combined with a fat saturation technique. The only difference between the second protocol and third protocol is that the second protocol has lower TE than the third protocol, which in turn offers more T1 and less PD properties. The increased T1 relaxation time may help to increase the image contrast within the different tissues in the MR image.

Bone models of the femur and tibia may be extracted from the MR images and appropriate anatomic reference landmarks may be identified. Full leg x-rays may be used to determine the mechanical axis alignment. Femoral and tibial cutting blocks may then be designed through computer aided design (CAD) modeling such that they conform to the bone models on one side for proper seating and have cutting slots at the appropriate resection depth and angle specific to the patient. The cutting blocks may be made from medical grade Nylon 12 using the EOSint P system. Since the surface geometries of these blocks are based on the patient's MR data set, clean data (properly differentiating between bone and cartilage and soft tissue) should be used to ensure the fit and functionality of the blocks.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A low profile patient specific cutting block for a knee, comprising:
    a plurality of bone interfacing portions configured to overlie portions of an end of a bone, the bone interfacing portions angularly offset from each other, a cutting slot oriented in a fixed position relative to the bone interfacing portions to direct a cutting tool at a fixed angle relative to the bone interfacing portions; and
    an anteriorly-facing exterior surface defining an index marking extending in a superior-inferior direction transverse to a longitudinal axis of the cutting slot to provide an indication of the orientation of the patient specific cutting block relative to the bone.

2. The low profile patient specific cutting block of claim 1, wherein the index marking comprises an M-L index axis positioned between a medial portion and a lateral portion of the patient specific cutting block.

3. The low profile patient specific cutting block of claim 1, wherein the index marking comprises a mechanical index axis positioned between a medial portion and a lateral portion of the patient specific cutting block, the mechanical index axis being generally aligned with a mechanical axis of the bone to provide the indication of the orientation of the patient specific cutting block relative to the bone.

4. The low profile patient specific cutting block of claim 1, wherein the index marking comprises a groove or score extending into the anteriorly-facing exterior surface of the patient specific cutting block.

5. The low profile patient specific cutting block of claim 1, wherein the index marking is positioned along a mid-portion of the patient specific cutting block between a medial portion and a lateral portion of the patient specific cutting block.

6. The low profile patient specific cutting block of claim 1, wherein a first of the bone interfacing portions extends in a first direction and a second of the bone interfacing portions extends in a second direction generally perpendicular to the first direction.

7. The low profile patient specific cutting block of claim 1, wherein the bone interfacing portions each have a surface that is generally a negative of the portion of the bone that the bone interfacing portion is configured to overlie, wherein a first of the bone interfacing portions is configured to overlie an anterior portion of the bone extending in a first direction, and wherein a second of the bone interfacing portions is configured to overlie another portion of the bone extending in a second direction generally perpendicular to the first direction.

8. The low profile patient specific cutting block of claim 7, wherein the first of the bone interfacing portions is configured to overlie an anterior face of the bone, and wherein the second of the bone interfacing portions includes a first portion configured to overlie a medial portion of the bone and a second portion configured to overlie a lateral portion of the bone.

9. The low profile patient specific cutting block of claim 1, wherein the patient specific cutting block further comprises a plurality of bosses each having a thickness and an aperture extending therethrough, the aperture having a diameter sized and configured to direct a pin therethrough, the thickness of the boss being greater than the diameter of the aperture.

10. The low profile patient specific cutting block of claim 1, wherein the bone interfacing portions further include medial and lateral paddles positioned medially and laterally at a posterior portion of the patient specific cutting block, and wherein the medial and lateral paddles each have a raised portion anteriorly oriented on the patient specific cutting block such that the paddles do not touch the tibia on an anterior proximal surface and do touch the tibia on a posterior proximal surface.

11. The low profile patient specific cutting block of claim 1, wherein the bone interfacing portions include an anterior portion generally positioned along the mid-portion of the patient specific cutting block, and wherein the bone interfacing portions further include medial and lateral paddles positioned medially and laterally at a posterior portion of the patient specific cutting block, and wherein the index marking extends along the anterior portion of the patient specific cutting block.

12. The low profile patient specific cutting block of claim 1, wherein the patient specific cutting block is a tibial cutting block and the cutting slot is medially offset relative to an anterior portion of the bone and is oriented entirely along a medial portion of the tibial cutting block and does not extend along a lateral portion of the tibial cutting block; and wherein the cutting slot opens in a direction facing the lateral portion of the tibial cutting block.

13. The low profile patient specific cutting block of claim 1, further comprising an epicondylar index marking extending in a medial-lateral direction to provide an indication of a rotational position of the patient specific cutting block relative to the bone.

14. The low profile patient specific cutting block of claim 13, wherein the patient specific cutting block is a femoral cutting block, and wherein the epicondylar index marking comprises a groove or score extending into the anteriorly-facing exterior surface of the femoral cutting block.

15. A low profile patient specific cutting block for a knee, comprising:
a plurality of bone interfacing portions configured to overlie portions of an end of a bone, the bone interfacing portions angularly offset from each other, wherein a first of the bone interfacing portions extends in an anterior-posterior direction and is adapted to overlie a proximal end portion of the bone, and wherein a second of the interfacing portions extends in a superior-inferior direction and is adapted to overlie an anterior portion of the bone;
a cutting slot oriented in a fixed position relative to the bone interfacing portions to direct a cutting tool at a fixed angle relative to the bone interfacing portions; and
wherein the patient specific cutting block comprises a tibial cutting block, and wherein the cutting slot is medially offset relative to an anterior portion of the bone and is oriented entirely along a medial portion of the tibial cutting block and does not extend along a lateral portion of the tibial cutting block.

16. The low profile patient specific cutting block of claim 15, wherein the cutting slot opens in a direction facing the lateral portion of the tibial cutting block.

17. The low profile patient specific cutting block of claim 15, wherein the first of the bone interfacing portions comprises a medial femoral paddle and a lateral femoral paddle, the medial femoral paddle configured to overlie a medial plateau of the bone, the lateral femoral paddle configured to overlie a lateral plateau of the bone; and wherein the second of the bone interfacing portions comprises an anterior portion configured to overlie an anterior face of the bone.

18. A low profile patient specific cutting block for a knee, comprising:

a plurality of bone interfacing portions configured to overlie portions of an end of a bone, the bone interfacing portions angularly offset from each other;
a cutting slot oriented in a fixed position relative to the bone interfacing portions to direct a cutting tool at a fixed angle relative to the bone interfacing portions; and
wherein the patient specific cutting block comprises a tibial cutting block, and wherein the cutting slot is medially offset relative to an anterior portion of the bone and is oriented entirely along a medial portion of the tibial cutting block and does not extend along a lateral portion of the tibial cutting block; and
wherein the bone interfacing portions each have a surface that is generally a negative of the portion of the bone that the bone interfacing portion is configured to overlie, and wherein a first of the bone interfacing portions extends in a first direction and a second of the bone interfacing portions extends in a second direction generally perpendicular to the first direction.

19. A low profile patient specific cutting block for a knee, comprising:
a plurality of bone interfacing portions configured to overlie portions of an end of a bone, the bone interfacing portions angularly offset from each other;
a cutting slot oriented in a fixed position relative to the bone interfacing portions to direct a cutting tool at a fixed angle relative to the bone interfacing portions; and
wherein the patient specific cutting block comprises a tibial cutting block, and wherein the cutting slot is medially offset relative to an anterior portion of the bone and is oriented entirely along a medial portion of the tibial cutting block and does not extend along a lateral portion of the tibial cutting block; and
wherein the patient specific cutting block includes an anteriorly-facing exterior surface defining an index marking extending in a superior-inferior direction transverse to a longitudinal axis of the cutting slot to provide an indication of the orientation of the patient specific cutting block relative to the bone.

20. The low profile patient specific cutting block of claim 19, wherein the index marking comprises a mechanical index axis positioned along a mid-portion of the patient specific cutting block between a medial portion and a lateral portion of the patient specific cutting block, the mechanical index axis being generally aligned with a mechanical axis of the bone to provide the indication of the orientation of the patient specific cutting block relative to the bone.

* * * * *